US006435176B1

(12) United States Patent
Berg et al.

(10) Patent No.: US 6,435,176 B1
(45) **Date of Patent: *Aug. 20, 2002**

(54) SPACER FOR USE WITH A METERED DOSE INHALER

(75) Inventors: Elna Birgitta Berg, Dalby; Hans Jörgen Nilsson, Lund, both of (SE)

(73) Assignee: Astra Aktiebolag, Sodertälje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/433,328

(22) PCT Filed: Jan. 23, 1995

(86) PCT No.: PCT/SE95/00058

§ 371 (c)(1), (2), (4) Date: Apr. 19, 1996

(87) PCT Pub. No.: WO95/20414

PCT Pub. Date: Aug. 3, 1995

(30) Foreign Application Priority Data

Jan. 27, 1994 (SE) ............................................ 9400257

(51) Int. Cl.[7] ............................................... A61M 11/00

(52) U.S. Cl. ............................ 128/200.23; 128/200.14; 128/203.23; 128/203.24; 604/57; 604/58

(58) Field of Search ....................... 128/200.14, 200.18, 128/200.22, 201.25, 203.12, 203.23, 203.24, 203.28, 200.23, 203.15, 204.17; 604/57, 58; 239/338; 118/629

(56) References Cited

U.S. PATENT DOCUMENTS

| | | | | |
|---|---|---|---|---|
| 2,534,636 A | * 12/1950 | Stirn | ..................... | 128/203.15 |
| 4,072,129 A | * 2/1978 | Bright et al. | ............... | 118/629 |
| 4,174,712 A | 11/1979 | Moren et al. | | |
| 4,829,996 A | * 5/1989 | Noakes et al. | ......... | 128/200.14 |
| 5,074,294 A | * 12/1991 | Chiesi | ................... | 128/200.14 |
| 5,427,089 A | * 6/1995 | Kraemer | ................ | 128/200.14 |
| 5,522,383 A | * 6/1996 | Calvest et al. | ......... | 128/203.15 |
| 5,619,984 A | * 4/1997 | Hodson et al. | ........ | 128/203.15 |

FOREIGN PATENT DOCUMENTS

| | | | | |
|---|---|---|---|---|
| EP | 0385212 | | 9/1990 | .......... A61M/15/00 |
| GB | 2110543 A | | 6/1983 | .......... A61M/15/00 |
| SE | 7612448-6 | | 2/1980 | .......... A61M/15/00 |
| WO | 91/00117 | * | 1/1991 | ............ 128/203.12 |
| WO | 9100117 | * | 1/1991 | .......... A61M/15/00 |
| WO | 9204070 | * | 3/1992 | .......... A61M/15/00 |
| WO | WO 93/16747 | | 9/1993 | |

* cited by examiner

*Primary Examiner*—John G. Weiss
*Assistant Examiner*—Michael Mendozn
(74) *Attorney, Agent, or Firm*—Fish & Richardson P.C.

(57) ABSTRACT

The present invention relates to a spacer for children primarily intended to be used in conjunction with a metered dose inhaler (MDI), said spacer having a generally oblong shape and being rotationally symmetrical around a central, longitudinal axis and being provided with an opening at each end located centrally in said axis for connection of an meterd dose inhaler respectively of a mouth-piece or similar. The spacer has a small total volume which is in the range between 50 and 400 ml, and the material in the spacer has a surface resitivity which is lower than $10^9$ Ohm, preferably lower than $10^6$ Ohm.

2 Claims, 1 Drawing Sheet

1
2
4
5
7
3

1
2
3
4
5
7

1
2
3
8

5
6
7

SPACER FOR USE WITH A METERED DOSE INHALER

TECHNICAL FIELD OF THE INVENTION

The present invention relates to an oblong spacer for children primarily intended to be used in conjunction with a metered dose inhaler (MDI), said spacer being rotationally symmetrical around a central, longitudinal axis and being provided with an opening at each end located centrally in said axis for connection of an MDI respectively a mouth-piece or similar.

BACKGROUND OF THE INVENTION

MDIS are containers with an actuating, metering valve containing a mixture of a pressurized propellant and a drug. When the valve is actuated, a dose of the drug/propellant mixture is ejected into the air and can be inhaled by a patient.

In order to alleviate the problems of a high oral deposition and the coordination difficulties associated with MDIS, different kinds of spacer devices have been developed. A spacer device includes a holding chamber adapted to be connected to the MDI at one end. The other end of the spacer is connected to or provided with a mouthpiece and/or a face mask through which a patient can inhale. When the valve is actuated, the dose of the drug/propellant mixture is sprayed into the spacer, resulting in a cloud of smaller particles in the respirable range (an aerosol) being contained in the chamber for a certain time, during which time larger particles, that is particles that normally would be deposited orally, are separated from the aerosol dose and deposited in the spacer. The propellant evaporates at the same time. The cloud of particles can be inhaled effortlessly by the patient.

The prior art devices of this kind are however exclusively designed for use in older children and adults. Their volume normally varies from 0.5 to 2 litres and they generally are made of a polymer material, for instance polycarbonate. They are often adapted for use in younger children. The reproducibility and age-dependency of their dose-delivery when used for the treatment of children is important, but these have not yet been ascertained. Theoretical models have predicted an increased lung deposition in small children due to the smaller airway calibre and a greater ventilation/kg, but in vivo documentation is sparse. Most of the available documentation in vivo of dose delivery from the prior art devices discusses the clinical response in wheezy children from inhalations of $\beta_2$-agonist. In these studies, the drug has been administered in doses considerably above the minimum effective dose. The response is therefore not critically dependent on reproducible delivery. The results from studies relating to these drugs further can not be extrapolated to the generation of a steroid aerosol, which has other micronizing and solubility characteristics.

Consequently there is a need for spacer delivery systems specially adapted to the treatment of young children. The need is particularly great in systems to be used in the administering of steroids due to the stricter demands on the reproducability and dosage accuracy for these drugs. A high utilisation of the substance also is desirable.

The volume of the spacer is critical since the aerosol is emptied from the chamber in an exponential manner. The inspiratory volume required to inhale the total dose of aerosol will be several times the spacer volume. The settling of particles limits the time available for inhalation. Since the inspirational capability of small children is smaller than the inspirational capability of adults, a reduction of the spacer volume might be indicated, for instance in the range of a few tidal breaths of an infant to reduce the time required for administration.

A reduced spacer volume will however contain an increased concentration of aerosols, and, accordingly, will require less time to empty. The fraction of airborne particles is however reduced due to impaction, adsorption, sedimentation and coagulation of the aerosol. This tendency will be aggravated if the spacer is made of a polymer material like polycarbonate, which may be charged by electrostatic forces, since the distance for each particle to the nearest wall will be smaller than in a prior art spacer, and the electrostatic forces will consequently have a greater influence.

The object of the invention consequently is to provide a spacer well adapted to the treatment of small children based on the above considerations.

SHORT DESCRIPTION OF THE INVENTION CONCEPT

The above object is achieved in that a spacer as described introductorily is designed to have a small total volume which is in the range between 50 and 400 ml, and in that the material in the spacer has a surface resitivity which is lower than $10^9$ Ohm, preferably lower than $10^6$ Ohm. In a most preferred embodiment the surface resistivity is lower than 1. Other preferred embodiments are set forth in the dependent claims.

BRIEF DESCRIPTION OF THE APPENDED DRAWINGS

DETAILED DESCRIPTION OF A PREFERRED EMBODIMENT OF THE INVENTION

Figure 1:
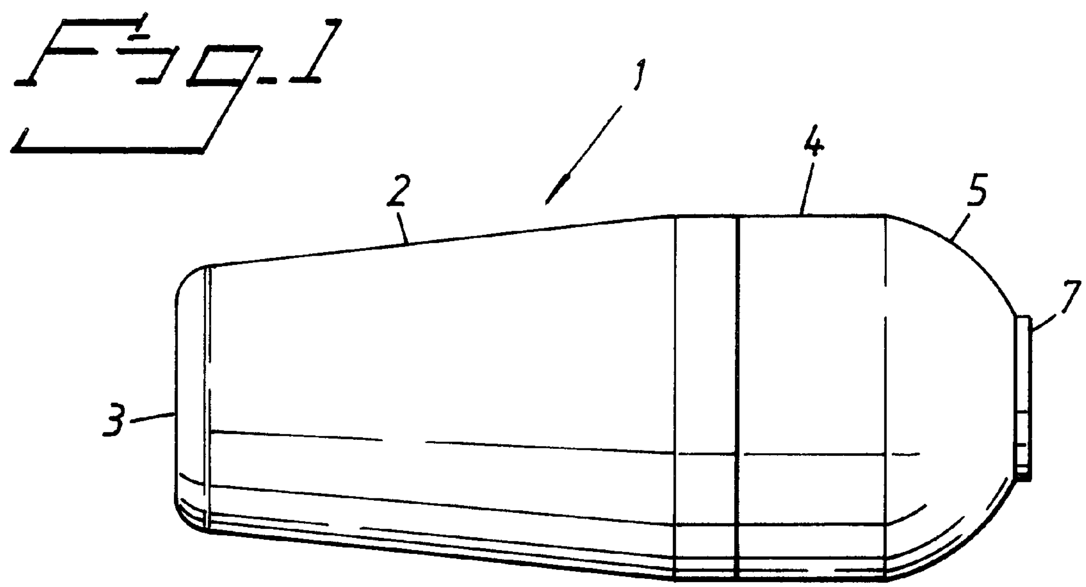
FIG. 1 shows a spacer according to the invention in a side view.
Figure 2:
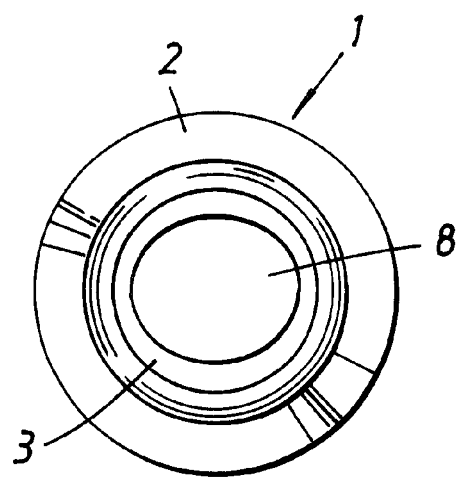
FIG. 2 illustrates the narrow end of the spacer to which an MDI is to be connected
Figure 3:
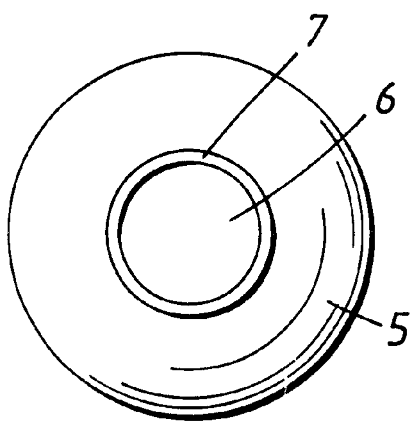
FIG. 3 shows the broad end of the spacer.

FIG. 1 shows the preferred spacer 1 which has an oblong shape with a slightly conically tapering first part 2 with a first end surface 3, a central, cylindrical part 4 and a substantially hemispherical second part 5. The junction between the surface 3 and the tapering part 2 is rounded. The spacer is circular in section and consequently is rotationally symmetrical. The overall length of the spacer is about 130 mm and the length of the tapering part is about 80 mm. The diameter of the end surface 3 is about 40 mm (the round part of the junction with the part 2 being disregarded), the diameter of the cylindrical part 4 being about 55 mm. The volume of the spacer is 220 ml. These dimensions are adapted to fit most small children although other dimensions are conceivable. The length of the spacer is adapted to standard MDIS in that the spacer is long enough to prevent particles within the respirable range from being sprayed onto the opposite walls of the device when the valve of the MDI is actuated.

The hemispherical part 5 is provided with a central opening 6 having a projecting, circumferential flange 7 for the attachment of a standard mouth-piece or a face mask. A two way valve may be connected between spacer and mouth-piece/mask.

The end surface 3 is also provided with a central opening 8 having an elliptical shape adapted to a standard mouth-piece adapter of a standard aerosol dispenser or MDI.

The spacer is made of stainless steel, which is a material having a surface resistivity which is well below the maximum surface resistivity at which the spacer is sufficiently conductive to function properly and at which the risk for electrostatic attraction of the respirable particles to the walls of the spacer is minimized.

The use of stainless steel will also result in a very robust spacer which consequently also in this respect is very well adapted to the use in smaller children.

In use, the mouth piece adapter of the MDI is connected to the corresponding end of the spacer and the mouth-piece with the two-way valve is connected to the other end. The two-way valve is designed to allow the inspirational air to flow through the spacer from the MDI to the mouthpiece but to prevent the expirational air from flowing from the mouth-piece, in this way creating a rectified inspiration through the spacer. The inspirational air is sucked through the mouth piece adapter of the MDI though the standard air openings provided therein for ordinary use without a spacer.

The rectified air flow in conjunction with the low risk for electrostatic influence on the respirable particles and the small volume of air which has to be inhaled will contribute to the deposition of a reasonably reproducable and accurate dosage in the desired locations in the lungs of the child, as well as also contributing to the achievement of the utilisation of a larger part of the drug than possible in standard prior art devices.

POSSIBLE MODIFICATIONS OF THE INVENTION

The invention of course can be modified in many ways within the scope of the appended claims.

The desired surface resistivity characteristics can be obtained in several ways.

Thus, it is possible to use most metals, any polymer materials having a surface resistivity below the desired values, polymers containing additives giving the desired chacteristics and polymers having been given the desired characteristics by means of a surface treatment.

What is claimed is:

1. A spacer for use with a metered dose inhaler (MDI), comprising a metal body which defines a chamber having a total volume of between 50 and 400 ml, wherein the body has a generally oblong shape which is rotationally symmetrical about a longitudinal axis and an opening at each end, one of the openings being adapted for connection to a metered dose inhaler.

2. The spacer of claim 1, wherein the body is composed of stainless steel.

* * * * *